US006984745B2

(12) United States Patent
Dougherty et al.

(10) Patent No.: US 6,984,745 B2
(45) Date of Patent: Jan. 10, 2006

(54) ENVIRONMENTALLY BENIGN LEAD ZIRCONATE TITANATE CERAMIC PRECURSOR MATERIALS

(75) Inventors: Thomas K. Dougherty, Playa Del Rey, CA (US); John J. Drab, Santa Barbara, CA (US)

(73) Assignee: Raytheon Company, Waltham, MA (US)

( * ) Notice: Subject to any disclaimer, the term of this patent is extended or adjusted under 35 U.S.C. 154(b) by 101 days.

(21) Appl. No.: 10/771,066

(22) Filed: Feb. 2, 2004

(65) Prior Publication Data
US 2005/0168916 A1 Aug. 4, 2005

(51) Int. Cl.
*C07F 3/00* (2006.01)
*C07F 7/00* (2006.01)
*C04B 35/49* (2006.01)
*B05D 5/12* (2006.01)
*C09K 3/00* (2006.01)

(52) U.S. Cl. .......................... 556/55; 556/105; 501/134; 427/126.3; 423/608; 423/618; 252/183.11

(58) Field of Classification Search ................. 556/55, 556/105; 501/134; 252/183.11; 427/126.3; 423/608, 618
See application file for complete search history.

(56) References Cited

U.S. PATENT DOCUMENTS

| | | | |
|---|---|---|---|
| 5,434,102 | A | 7/1995 | Watanabe |
| 5,439,845 | A | 8/1995 | Watanabe |
| 5,721,009 | A | 2/1998 | Dougherty et al. |
| 6,054,600 | A | 4/2000 | Dougherty et al. |
| 6,149,968 | A * | 11/2000 | Shimada ..................... 427/100 |
| 6,303,804 | B1 | 10/2001 | Dougherty et al. |
| 6,316,651 | B1 | 11/2001 | Dougherty et al. |
| 2001/0041216 | A1 * | 11/2001 | Sakamaki et al. .......... 427/100 |

FOREIGN PATENT DOCUMENTS

WO WO 93/12538 6/1993

OTHER PUBLICATIONS

Zai, M.H.M., et al., "Highly (111) Oriented Lead Zirconate Titanate Thin Films Deposited Using a Non-Polymeric Route", *Thin Solid Films*, vol. 394, 2001, pp. 97-101.

Wright, J.S. and L.F. Francis, "Processing of Piezoelectric Properties of MOD PZT Film and PZT/Polymer Composites", *Materials Research Society Symposium #433*, 1996, pp. 357-362.

Mantese, J.V., et al., "Metaloriganic Deposition (MOD): A Nonvacuum, Spin-on, Liquid-Based, Thin Film Method", MRS Bulletin, Oct. 1989, pp. 48-53.

Vest, G.M., et al., "Synthesis of Metallo-Organic Compounds for MOD Powders and Films", *Materials Research Society Symposium Proceedings*, vol. 60, 1986, pp. 35-42.

Klee, M., et al., "Processing and Electrical Properties of PZT Films: Comparison of Metallo-Organic Decomposition and Sol-Gel Processes", Journal of Applied Physics, vol. 72 (4), 1992, pp. 1566-1576.

Schwartz et al., "A Comparison of Diol and Methanol-Based Chemical Solution Routes for PZT Thin Film Fabrication", *Integrated Ferroelectrics*, vol. 18, 1977, pp. 275-286.

* cited by examiner

*Primary Examiner*—Porfirio Nazario-Gonzalez
(74) *Attorney, Agent, or Firm*—John E. Gunther; Leonard A. Alkov; Karl A. Vick

(57) ABSTRACT

The synthesis, processing and test of improved lead zirconate titanate (PZT) precursor materials useful for making bulk, thick films and thin films of PZT are provided. PZT is an oxide ceramic extensively used for its piezoelectric properties. A variety of devices made from piezoelectric PZT are known. A soluble spin-on precursor is provided that is compatible with and soluble in non-toxic and environmentally benign solvents (including water), has high stability and long shelf life, and provides high quality PZT films.

17 Claims, 1 Drawing Sheet

FIG. 1
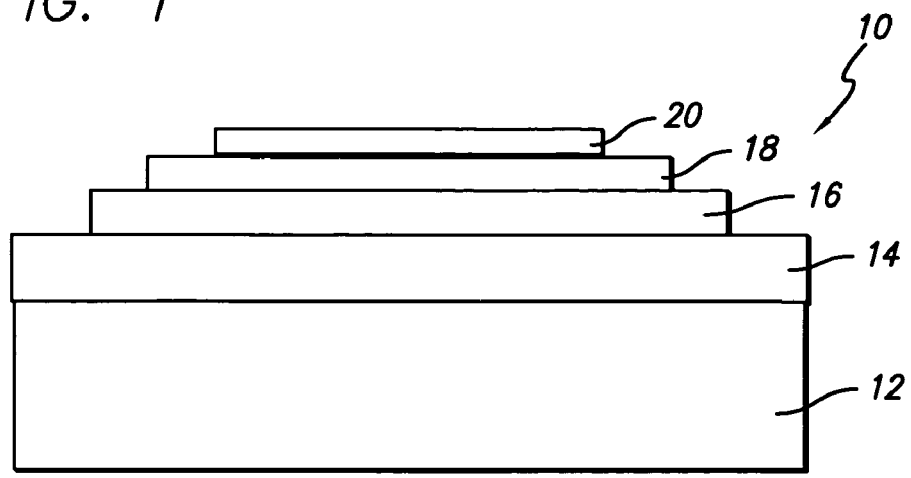
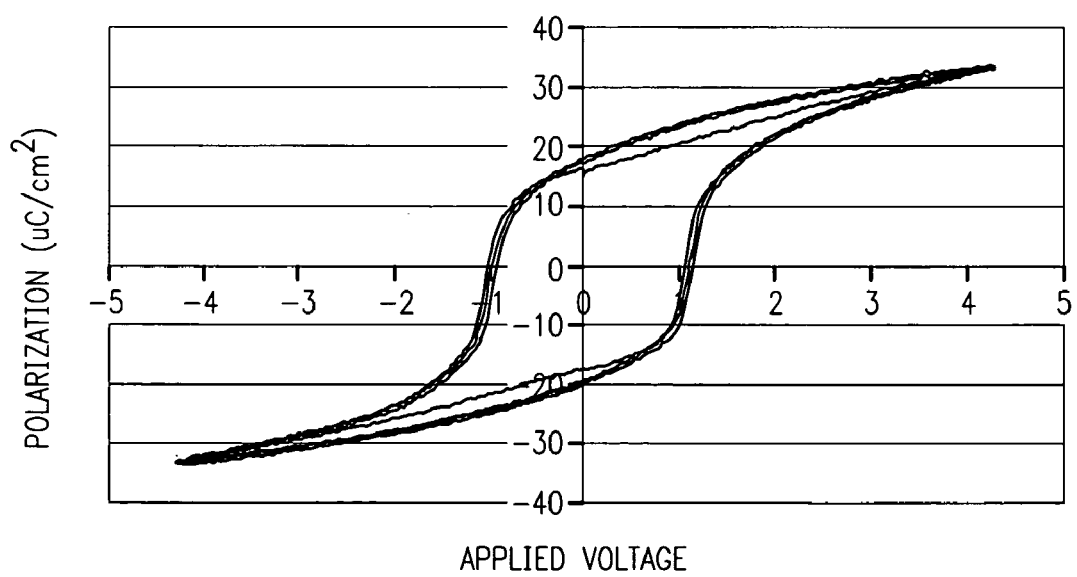
FIG. 2

ENVIRONMENTALLY BENIGN LEAD ZIRCONATE TITANATE CERAMIC PRECURSOR MATERIALS

TECHNICAL FIELD

The present invention relates generally to improved ceramic precursors and specifically to ceramic precursors for fabricating lead zirconate titanate materials.

BACKGROUND ART

Lead zirconate titanate (PZT) is an oxide ceramic extensively used for its piezoelectric properties. Devices made from piezoelectric PZT include actuators and transducers as well as MEMS (microelectromechanical systems) devices such as lab on a chip (fluidic devices), surface acoustic wave (SAW) devices, tunable filters, RF switches, and all of the other devices MEMS promises. PZT is also widely used for ferroelectric applications such as non-volatile memories, electro-optic applications such as light valves, and applications in pyroelectric infrared detectors are also wide-spread.

Present processes for preparing PZT precursor materials suffer from a variety of different problems. One example of such a problem is the sale and use of water-reactive, limited shelf life PZT precursors that are solution processable only in toxic, flammable and hazardous solvents; see, for example, Alfa Aesar Product 36575 and 39758, Chemat Product PZT9103, and PZT Solution from Inostek, Korea.

Another example of such a problem is the processing of precursors in toxic solvents, employing large quantities of decomposable organics; see, for example, M. H. M. Zai et al, "Highly (111) oriented lead zirconate titanate thin films deposited using a non-polymeric route," *Thin Sold Films*, Vol. 394, pp. 97–101 (2001), who discuss metal-organic decomposition (MOD) deposition methods for PZT and the use of their new precursor to make PZT thin films. It appears that their precursors are most likely water-reactive (although not water-soluble).

Still another example of process problems is the tedious multi-step route to a PZT MOD precursors disclosed by J. S. Wright and L. F. Francis in "Processing of Piezoelectric properties of MOD PZT film and PZT/Polymer composites," *Materials Research Society Symposium* # 433, pp. 357–362 (1996).

The MOD process typically involves the synthesis of thin film ceramics from metal organic acid salts (mostly aliphatic acids such as neo-decanoic acid or 2-ethylhexanoic acid). The MOD process is described in, for example, (1) U.S. Pat. No. 5,721,009, "Controlled Carbon Content MOD Precursor Materials Using Organic Acid Anhydride," issued to Thomas K. Dougherty et al on Feb. 24, 1998; (2) J. V. Mantese et al, "Metalorganic Deposition (MOD): A Nonvacuum, Spin-on, Liquid-Based, Thin Film Method," *MRS Bulletin*, pp. 48–53 (October 1989); (3) WO 93/12538, "Process for Fabricating Layered Superlattice Materials," filed in the names of Carlos A. Paz de Araujo et al, published on 24 Jun. 1993; (4) U.S. Pat. No. 5,434,102 (issued on Jul. 18, 1995) and U.S. Pat. No. 5,439,845 (issued on Aug. 8, 1995), to Hitoshi Watanabe al and both entitled "Process for Fabricating Layered Superlattice Materials and Making Electronic Devices Including Same"; and (5) G. M. Vest et. al, "Synthesis of Metallo-Organic Compounds for MOD Powders and Films," *Materials Research Society Symposium Proceedings*, Vol. 60, pp. 35–42 (1986).

The present inventors and associates have continued their work in this area, culminating in (1) U.S. Pat. No. 6,054,600, "Non-Toxic Solvent Soluble Group IV and V Metal Acid Salt Complexes Using Polyether Acid Anhydrides," issued to T. Kirk Dougherty et al on Apr. 25, 2000; (2) U.S. Pat. No. 6,303,804, "Environmentally Benign Bismuth-Containing Spin-on Precursor Materials," issued to T. Kirk Dougherty et al on Oct. 16, 2001; and (3) U.S. Pat. No. 6,316,651, "Environmentally Benign Group II and Group IV or V Spin-on Precursor Materials," issued to T. Kirk Dougherty et al on Nov. 13, 2001. The contents of these patents are incorporated herein by reference.

With specific regard to PZT materials, M. Klee et al in "Processing and Electrical Properties of PZT films. Comparison of metallo-organic decomposition and sol-gel processes," *Journal of Applied Physics*, Vol. 72(4), pp. 1566–1576 (1992) compare the MOD and sol-gel process for PZT films.

Schwartz et.al in "A Comparison of Diol and Methanol-based Chemical Solution Routes for PZT Thin Film Fabrication," *Integrated Ferroelectrics*, Vol. 18, pp 275–286 (1977) discuss propanediol-based precursors which have issues with uniformity, coating stability, and shelf life.

There remains a need for a soluble spin-on precursor which is compatible and soluble in non-toxic and environmentally benign solvents (including water), has unlimited stability and shelf life, and provides high quality PZT films and materials.

DISCLOSURE OF INVENTION

In accordance with the present invention, a water-stable and water-soluble ceramic precursor containing lead, zirconium and titanium is provided.

Further in accordance with the present invention, a metal acid salt complex comprising (1) lead, zirconium, and titanium, and (2) a polyether acid is provided.

Still further in accordance with the present invention, a method of preparing a metal acid salt complex is provided. The method comprises combining (1) a mixture of metal alkoxides comprising zirconium and titanium alkoxides, (2) a polyether acid anhydride, and (3) a lead polyether acid salt complex.

Yet further in accordance with the present invention, a process is provided for preparing a metal acid salt complex comprising a zirconium polyether acid salt complex, a titanium polyether acid salt complex, a polyether acid anhydride, and a lead polyether acid salt complex. The process comprises:

preparing the polyether acid anhydride from its corresponding polyether acid;

reacting a zirconium alkoxide and a titanium alkoxide with the polyether acid anhydride to form the zirconium polyether acid salt complex and the titanium polyether acid salt complex, respectively;

reacting a polyether acid with a lead salt of a labile acid to form the lead polyether acid salt complex; and combining said lead polyether acid salt complex with said zirconium and titanium salt complexes.

Finally, in accordance with the present invention, a device that includes lead zirconate titanate as its active component is provided, wherein the lead zirconate titanate precursor is prepared by the preceding process. A variety of PZT-based devices are contemplated, including, but not limited to, actuators and transducers as well as MEMS (microelectromechanical systems) such as lab on a chip (fluidic devices), surface acoustic wave (SAW) devices, tunable filters, RF switches, and the like. PZT is also widely used for ferroelectric applications such as non volatile memories, electro-optic applications such as light valves, and pyroelectric detectors for imaging over a wide range of wavelengths including infrared imaging.

The present invention provides for improved and environmentally benign PZT precursors and processing of PZT. Electrical performance of capacitors made from this material is excellent. Prior art liquid precursors for PZT (some commercially available) are either water-sensitive and have limited shelf life and/or must be processed in toxic solvents and contain large quantities of decomposable organics that potentially complicate processing and deteriorate device quality.

The present invention provides for a soluble and easily processable PZT precursor which is compatible and soluble in non-toxic and environmentally benign solvents (including water), has high stability and a very long shelf life. This precursor contains relatively few decomposable organics, and is capable of producing very high quality PZT films.

BRIEF DESCRIPTION OF THE DRAWINGS

FIG. 1 is a side elevational view of a ferroelectric PZT capacitor that benefits from the production of PZT films, as disclosed herein; and FIG. 2, on coordinates of polarization (in microCoulombs/cm$^2$) and applied voltage (in volts), is a plot of hysteresis data obtained from a ferroelectric PZT capacitor having the structure of FIG. 1, with the PZT thin film prepared in accordance with the invention.

BEST MODES FOR CARRYING OUT THE INVENTION

The embodiments herein are directed to providing improved PZT materials compatible with less toxic solvents useful for manufacture of a variety of PZT-based products.

Although the previous patents describe some of the compounds and processes for production of PZT films (for example, U.S. Pat. No. 6,054,600 discloses titanium), there do not appear to be any references in the prior art that specifically describe the lead or zirconium salt compounds provided herein, or the formulation of the compounds to provide a water-soluble and stable PZT precursor, or processing of the PZT precursor into ferroelectric PZT capacitors made therefrom.

The present invention allows the production of improved metal oxide precursors for ceramics and metal oxide thin films, specifically, for lead zirconate titanate (PZT) materials. It extends the use of the polyether acids as precursor salts to these metal oxides. Examples of useful polyether acids include methoxyacetic acid, methoxyethoxyacetic acid, and methoxyethoxyethoxyacetic acid. Essentially, the polyether acids useful in the practice of the present invention are polyether acids of ethylene glycol, having the formula $$CH_3O(CH_2CH_2O)_xCH_2COOH$$

where x is an integer of 0 to 2.

The use of polyether acids for the formation of PZT films has not been previously shown in the prior art. The ceramic precursors disclosed herein are soluble in more common and much less toxic solvents than the prior art.

The general synthetic route to providing lead, zirconium, and titanium polyether acid metal acid salt complexes is as follows:

1. Prepare a polyether acid anhydride from the corresponding polyether acid by combining the polyether acid with a dehydrating agent.
2. Prepare a metal acid salt complex of each of titanium and zirconium by combining the polyether acid anhydride and the respective metal alkoxide.
3. Prepare a metal acid salt complex of lead by combining a polyether acid with a lead salt of a labile acid.

The dehydrating agent used in the first reaction may comprise any of the known dehydrating agents used to convert organic acids to the corresponding anhydride. Examples include acetic anhydride and dicyclohexylcarbodiimide.

The thermodynamics of the second reaction tends to be mildly exothermic and the temperature should be carefully controlled and monitored, typically between about 40° and 120° C., and preferably, at or near the higher end of the range, which facilitates reaction completion in a convenient time.

The metal alkoxide used in the second reaction may comprise any of the known zirconium and titanium alkoxides. The alkoxides are given by the general formula $$(R-O)_4-Me$$

where R is substituted and unsubstituted straight or branched alkyls ($C_1$ to $C_8$) and aryls, and Me is zirconium or titanium.

The zirconium and titanium acid salt complexes that are formed are represented by the formula $$Metal\left(O-\underset{O}{\underset{\|}{C}}-CH_2-\left(O-CH_2CH_2\right)_p-O-\right)_4$$

where "metal" is either zirconium or titanium and p is independently 0, 1 or 2 for each of the four ligands.

The lead salt used as starting material for the third reaction can be any of the commonly available lead salts, for example, lead acetate or lead carbonate. The third reaction may be facilitated by heat, e.g., within the range of about 40° and 120° C., and is benefited by the removal of by-product, such as by evolution of gas or distillation. For example, where the starting material is lead carbonate, the evolution of the by-product carbon dioxide facilitates the reaction. Where the starting material is lead acetate, the distillation of the by-product acetic acid facilitates the reaction.

The lead acid salt complex that is formed is represented by the formula $$\diagdown O\left(\diagdown\diagup O\right)_m \underset{O}{\underset{\|}{C}} O-Pb-O \underset{O}{\underset{\|}{C}} \left(O\diagdown\diagup\right)_n O\diagup$$

where n and m are independently 0, 1 or 2.

The PZT devices formed herein are advantageously employed in a variety of devices; such PZT-based devices are well known. An example of one such device is a thin film ferroelectric PZT capacitor.

FIG. 1 illustrates an embodiment of such a ferroelectric PZT capacitor 10. On a substrate 12 is formed an insulating layer 14. A bottom electrode 16 is formed on the insulating layer 12. A PZT layer 18 is formed on the bottom electrode 16. A top electrode 20 is formed on the PZT layer 18. Electrical contact (not shown), using conventional electrically conducting materials, such as a metal, is made to the bottom electrode 16 and top electrode 20.

As an example, the substrate 12 comprises silicon, doped with phosphorus to a resistivity of about 3 to 15 ohm-cm, although any process-compatible substrate material may be employed in the practice of the present invention.

The insulating layer 14, in the case of a silicon substrate 12, is advantageously an oxide of silicon, $SiO_2$, and serves to provide electrical insulation from the substrate 12. In this connection, any insulating layer may be used in the practice of the present invention. The thickness of the insulating layer 14 is on the order of 5,000 Å.

The bottom electrode 16 comprises, for example, a multi-layer structure of platinum on tantalum, with the total thickness being about 1,850 Å, although any electrically conducting electrode material compatible with the process may be used in the practice of the present invention. The PZT layer 18 is formed to a thickness of, for example, 1,400 Å. The top electrode 20 comprises, for example, platinum having a thickness of about 1,100 Å. The thicknesses of the bottom electrode 16, the PZT layer 18, and top electrode 20 are not critical to the practice of the present invention, and are simply those commonly employed with PZT-based devices. Further details of such ferroelectric PZT capacitors may be found in, for example, the Klee reference noted above.

Devices made from piezoelectric PZT include actuators and transducers as well as MEMS (microelectromechanical systems) such as lab on a chip (fluidic devices), surface acoustic wave (SAW) devices, tunable filters, RF switches, and the like. PZT is also widely used for ferroelectric applications such as non-volatile memories, electro-optic applications such as light valves and in pyroelectric detectors.

The following text provides the details of the synthesis of PZT precursor materials. The materials are soluble in non-toxic solvents, including water.

EXAMPLES

Synthesis of Methoxyethoxy Acetic Anhydride (CAS 132806-43-0).

A mixture of methoxyethoxyacetic acid (CAS 16024-56-9, 1022 g, 7.6 mol) and acetic anhydride (453 g, 4.4 mol) was heated with stirring in a 2 L 3-neck flask equipped with a 6 inch Vigreux distillation column. The internal pressure of the reactor was brought to 55 torr using a vacuum pump and manostat and material was gently distilled by heating to give about 420 grams of distillate (b.p. 45°–60° C.), identified as a mixture of acetic acid and acetic acid anhydride. The reactor was charge with an additional 351 grams of acetic anhydride and the process repeated. This process was repeated once again with an additional 270 gram of acetic anhydride. The acetic acid and acetic anhydride were again removed by distillation, the pressure was reduced, and the product was carefully distilled after a forerun. The product was collected at 120°–130° C. at 50 microns to give the title compound, 835 g (88% yield) of pure title compound. IR (thin film) 2928, 2886, 2826, 1837, 1678, 1121, 1050. $^{13}C$ NMR($CDCl_3$) 166.0, 71.7, 70.8, 68.7, 58.8. $^{1}H$ NMR ($CDCl_3$) 4.31 (s, 4H), 3.75 (m, 4H), 3.58 (m, 4H), 3.38 (s, 6H).

Synthesis of Lead (II) Methoxyacetate.

A 500 mL round bottom flask was charged with lead (II) acetate (Alfa 10719, 50.4 g, 0.133 mol) and methoxyacetic acid (209.8 g, 2.3 mol). The contents of the reactor were heated to 100° C. with an external oil bath and the volatile materials were distilled at 100 to 50 torr, head temperature to 65° C. The distillate was identified as a mixture of acetic acid and methoxyacetic acid. The pressure was further reduced and the excess methoxyacetic acid was removed. The title product was isolated as a colorless viscous liquid and diluted in water to give 87.6 grams of product (31% lead). Thermo-gravimetric analysis in air to 800° C. gave 32.5% lead oxide, calculated 32.8%. IR (thin film) 3441, 2943, 2834, 1731, 1585, 1428, 1202, 1114.

It will be appreciated by those skilled in this art that in the course of this work, it was found that the larger lead polyether acetate salts (e.g., lead methoxyethoxy acetate and lead methoxyethoxyethoxy acetate) form white solids that were difficult to dissolve. These were made analogously to the above by substituting the larger organic acid. Thus, the smaller lead methoxyacetate appears to be best as a soluble lead precursor.

Synthesis of Zirconium (IV) Methoxyethoxyacetate.

A 500 mL round bottom flask was charged with zirconium (IV) n-propoxide (AlfaAesar 22989, 70% in n-propanol, 55.9 g, 0.13 mol) and methoxyethoxyacetic anhydride (187.1 gram, 0.75 mol). The contents of the reactor were heated to 100° C. with an external oil bath and after 1 hour a small aliquot of the material was analyzed by gas chromatography, showing no excess anhydride. A total of an additional 38 grams of anhydride was added, at which point an excess of anhydride was established. The anhydride was most likely being consumed by the excess propanol in the zirconium starting material to make additional n-propylester of methoxyacetic acid. After the reaction was judged complete, most of the volatile materials were distilled away at reduced pressure to give a brown mobile liquid (154.5 g, 7.8% zirconium, stable in water). Thermo-gravimetric analysis in air to 800° C. gave 10.5% zirconium oxide, calculated 10.8%. IR (thin film) 2930, 2888, 1760, 1592, 1457, 1146, 1121.

Synthesis of Titanium (IV) Methoxyethoxyacetate.

In a 250 mL round bottom flask was placed titanium isopropoxide (Aldrich 20,527-3, 35.0 g, 0.123 mol) and methoxyethoxyacetic anhydride (125.5 g, 0.50 mol). The contents of the flask were heated to 80° C. with an external oil bath and a small aliquot of the reaction mixture was analyzed by gas chromatography. No anhydride was found. An additional 12.8 grams of anhydride was added, at which point gas chromatographic analysis showed that a small excess of anhydride was present. A small amount of volatile components was removed by vacuum distillation to leave the product as a mixture in the 2-propylester of methoxyethoxyacetic by-product. (This ester has been found to be an excellent co-solvent for the PZT precursors and was left in the product to facilitate formulation of the precursors for thin film spin on deposition in subsequent processing.)

The mass of water-stable product mixture was 161 grams (3.65% titanium). Thermo-gravimetric analysis in air to 800° C. gave 5.94% titanium dioxide, calculated 6.09%. IR (thin film) 2983, 2932, 2886, 1839, 1750, 1212, 1147, 1110.

Formulation of Water-Stable PZT Precursor.

A water-stable PZT precursor was formulated from the above-synthesized lead, zirconium and titanium materials. The solution precursor contained (1) the lead methoxy acetate material (8.350 g, 2.588 g lead, 12.5 mg atom), (2) the zirconium methoxyethoxy acetate (4.929 g, 0.38 g zirconium, 4.2 mg atom), (3) the titanium methoxyethoxy acetate mixture in ester (8.481 g, 0.309 g titanium, 6.5 mg atom), (4) 9.157 g water, and (5) 0.221 g TRITON X-100, a surfactant. The formulated mixture had a calculated percent solids of 12% as PZT oxide. The mole ratio of lead to zirconium to titanium was calculated as PZT 1.2:0.4:0.6.

Processing of Described PZT Precursor to PZT Thin Films.

1. Substrate Preparation Including Bottom Electrode Evaporation.

A conventional 20 mil (0.020 inch) thick silicon wafer was prepared with a surface layer of 5,000 Å of a wet thermal oxide (silicon oxide). A platinum electrode was then deposited using the process described in co-pending application Ser. No. 10/147,093, filed May 15, 2002.

2. Deposition and Firing of PZT Thin Film on Electroded Substrate.

The wafers from the preceding paragraph were coated with the PZT solution described above using a 2500 rpm 120 sec spin. After coating, the wafer was slowly lowered onto a 150° C. hot plate and baked for 5 minutes.

After spin-coating and hot plate baking, the wafer was fired in a furnace with flowing $O_2$ at 650° C. The process was repeated a total of three times to give a thin film PZT layer of about 2,400 Å thickness.

3. Application of Top Electrode.

A platinum top electrode was deposited by DC sputtering. The wafer was patterned with a capacitor mask and ion milled (the mill process etched the top electrode and PZT to expose the bottom electrode).

A conventional post-etch recovery anneal was performed on the capacitor wafers to square the hysteresis properties. The anneal performed on the wafers was again a 650° C. one hour oxygen cycle.

4. Electrical Test.

The devices were tested on an analytical prober. Contact to the top electrode was made directly with a probe tip, while contact to the bottom electrode was made by scratching through the PZT layer with a second probe tip. The capacitance-voltage (CV) characteristics were measured using a HP4275A LCR Meter at 100 KHz using a modulation voltage of 35 mV over a wide range of bias voltages. The current-voltage (IV) characteristics were measured using a HP 4145B Semiconductor Parameter Analyzer over the range of −3.5 V to +3.5 V. For a typical 10 mil (0.010 inch) diameter shadow mask capacitor, the capacitance ranged from 1.69 pF at 0 V to 0.75 pF at 6.5 V. The maximum leakage current was measured to be 100 nA at 3.5 V. Low frequency (4 Hz) single shot hystersis loops were measured using a Radiant Technologies RT-66a ferroelectric test station in manual mode. This hysteresis data is shown in the plot depicted in FIG. 2. The series of hysteresis loops plotted in FIG. 2 shows excellent performance with a switchable polarization (2Pr) of ~38 $\mu C/cm^2$ and a coercive voltage (Vc) of around 1 V. Saturation is achieved at around 3 V with a saturated polarization (Psat) of about 34 $\mu C/cm^2$ at 4.5 V.

Thus has been described the synthesis and formulation of a new water-stable, long shelf life, PZT precursor and the processing of this material into ferroelectric capacitor thin films.

INDUSTRIAL APPLICABILITY

The use of the PZT precursors disclosed herein is expected to find applications in the fabrication of PZT-based devices.

What is claimed is:

1. A water-stable and water-soluble ceramic precursor containing lead, zirconium, and titanium polyether acid salt complexes.

2. The ceramic precursor of claim 1 wherein said polyether acid is given by the formula

$$CH_3O(CH_2CH_2O)_xCH_2COOH$$

where x is an integer of 0 to 2.

3. The ceramic precursor of claim 1 wherein
   (a) said lead polyether acid salt is represented by the following structure

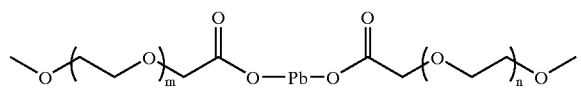

where n and m are independently 0, 1 or 2; and
   (b) said zirconium and titanium polyether acid salts are represented by the following structures:

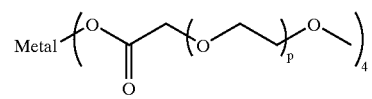

where "metal" is either zirconium or titanium and p is independently 0, 1 or 2 for each of the four ligands.

4. A metal acid salt complex comprising (1) lead, zirconium, and titanium, and (2) a polyether acid.

5. The metal acid salt complex of claim 4 wherein said polyether acid is given by the formula

$$CH_3O(CH_2CH_2O)_xCH_2COOH$$

where x is an integer of 0 to 2.

6. The metal acid salt complex of claim 5 comprising lead in its II oxidation state and zirconium and titanium in their IV oxidation state.

7. The metal acid salt complex of claim 6 wherein
   (a) said lead acid salt complex is represented by the formula

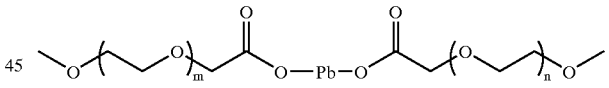

where n and m are independently 0, 1 or 2; and
   (b) said zirconium and titanium acid salt complexes are represented by the formula

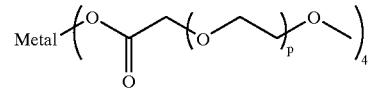

where "metal" is either zirconium or titanium and p is independently 0, 1 or 2 for each of the four ligands.

8. A method of preparing a metal acid salt complex, said method comprising combining (1) a mixture of metal alkoxides comprising zirconium and titanium alkoxides, (2) a polyether acid anhydride, and (3) a lead polyether acid salt complex.

9. The method of claim 8 wherein said polyether acid anhydride is prepared from the corresponding polyether acid by combining said polyether acid with a dehydrating agent.

10. The method of claim 8 wherein said polyether acid salt complex of lead is prepared by combining a polyether acid with a lead salt of a labile acid.

11. The method of claim 8 wherein said polyether acid is given by the formula

CH₃O(CH₂CH₂O)ₓCH₂COOH where x is an integer of 0 to 2.

12. The method of claim 11 wherein
(a) said lead acid salt complex is represented by the formula

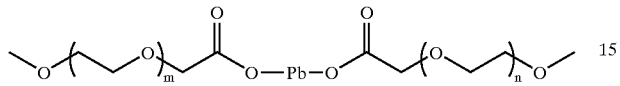

where n and m are independently 0, 1 or 2; and
(b) said zirconium and titanium acid salt complexes are represented by the formula

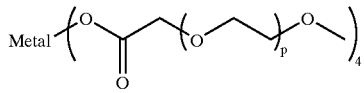

where "metal" is either zirconium or titanium and p is independently 0, 1 or 2 for each of the four ligands.

13. A process for preparing a metal acid salt complex comprising a zirconium polyether acid salt complex, a titanium polyether acid salt complex, a polyether acid anhydride, and a lead polyether acid salt complex, said process comprising:

preparing said polyether acid anhydride from its corresponding polyether acid;

reacting a zirconium alkoxide and a titanium alkoxide with said polyether acid anhydride to form said zirconium polyether acid salt complex and said titanium polyether acid salt complex, respectively;

reacting a polyether acid with a lead salt of a labile acid to form said lead polyether acid salt complex; and combining said lead polyether acid salt complex with said zirconium and titanium salt complexes.

14. The method of claim 13 wherein said polyether acid is given by the formula

CH₃O(CH₂CH₂O)ₓCH₂COOH where x is an integer of 0 to 2.

15. The method of claim 14 wherein
(a) said lead acid salt complex is represented by the formula

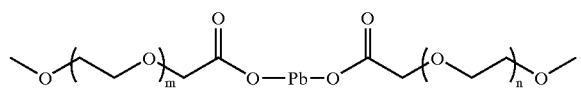

where n and m are independently 0, 1 or 2; and
(b) said zirconium and titanium acid salt complexes are represented by the formula

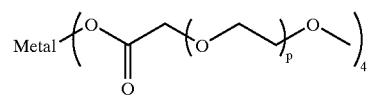

where "metal" is either zirconium or titanium and p is independently 0, 1 or 2 for each of the four ligands.

16. The process of claim 13 wherein both said reacting steps are carried out at an elevated temperature within a range of 40° to 120° C.

17. The process of claim 14 wherein said combining step is carried out at an elevated temperature within a range of 40° to 120° C.

* * * * *